United States Patent [19]  [11] Patent Number: 4,727,020
Recktenwald  [45] Date of Patent: Feb. 23, 1988

[54] METHOD FOR ANALYSIS OF SUBPOPULATIONS OF BLOOD CELLS

[75] Inventor: Diether J. Recktenwald, Cupertino, Calif.

[73] Assignee: Becton, Dickinson and Company, Franklin Lakes, N.J.

[21] Appl. No.: 705,252

[22] Filed: Feb. 25, 1985

[51] Int. Cl.⁴ .................... C12Q 1/04; C12Q 1/68; G01N 33/554; G01N 33/577

[52] U.S. Cl. ........................... 435/6; 356/39; 356/73; 435/7; 435/29; 435/34; 436/63; 436/72; 436/501; 436/519; 436/548; 436/800; 436/827; 935/110

[58] Field of Search ............... 436/519, 548, 63, 172, 436/501, 800, 827; 935/110; 435/6, 7, 24, 34; 356/39, 73

[56] References Cited

U.S. PATENT DOCUMENTS 3,883,247  5/1975  Adams .......................... 356/39

OTHER PUBLICATIONS

H. M. Shapiro, *Cytometry*, 3, 227–243, 1983.

M. R. Melino et al., Journ. Immunol. 130, 1843–1847, 1983.

R. A. Miller et al., Journ. Immunol. 133, 3408–3414, 1984.

*Primary Examiner*—Sidney Marantz
*Assistant Examiner*—David A. Saunders
*Attorney, Agent, or Firm*—Robert M. Hallenbeck

[57] ABSTRACT

A method for identifying and enumerating cells of a subclass of blood cells in relation to cells of another subclass of blood cells is provided. In the method a first subclass of blood cells is selectively tagged by incubating an aliquot of a blood sample with a first tagging agent. A second subclass of blood cells is selectively tagged by incubating the aliquot with a second tagging agent. The aliquot is then passed, without lysing of any subclasses of blood cells which are not of interest, substantially a cell at a time through an area of optical stimulation for the tagging agents. Light emitted by the tagging agents is detected, the detection being limited by gating to a threshold value related to a predetermined intensity of light by one of the tagging agents. Cells of the subclass are differentiated based on occurrence of emitted light from the tagging agents.

21 Claims, 9 Drawing Figures

METHOD FOR ANALYSIS OF SUBPOPULATIONS OF BLOOD CELLS

BACKGROUND OF THE INVENTION

1. Field of the Invention

The present invention relates to a method and apparatus for distinguishing and identifying subpopulations of cells in a sample without interference from other cells or particles in the same, and more particularly, related to a method and apparatus for distinguishing and quantifying blood cells or subpopulations of blood cells in a sample without interference from other blood cells, particularly red blood cells.

2. Description of the Prior Art

The leucocyte (white blood cell) population in blood is defined by a number of subclasses which play distinct roles in the immune response. For example, the relative number of cells in various lymphocyte subclasses is likely to change in disease states. Hence, identification of cells of the various subclasses provides an analytic tool that has been found to be of great value in the diagnosis of various diseases and the monitoring of treatment for the disease.

It is known that at least several particular subclasses of functionally distinct lymphocytes can be identified by antibodies, particularly monoclonal antibodies, to antigenic determinants on the cell surface. In particular, there has been considerable academic and clinical interest in the identification of the various subclasses of T-lymphocytes. T-lymphocytes are characterized by identifiable antigenic determinants on their surface which distinguish the cells of that subclass from other blood cells and from the cells of other lymphocyte subclasses. Hence interest is high in developing rapid methods for the analysis of white blood cells, particularly the analysis of lymphocytes and the T-cell subclass of lymphocytes.

T cells are divided into at least several subtypes, termed "helper", "suppressor", and "cytotoxic" T cells, which have the function of (respectively) promoting a reaction, suppressing a reaction, or killing (lysing) foreign cells. The ability to identify subtypes of T cells is important for diagnosis or treatment of various immunoregulatory disorders or conditions.

The preparation of a blood sample for analysis of the leucocyte (white blood cell) populations has usually been based on the apparent need to separate the white blood cells from the erythrocyte (red blood cell) population. The red blood cells outnumber the white blood cells by a factor of about 1000 to 1. The overwhelming prominence of red blood cells has led investigators to conclude that the red blood cells must be removed from the sample prior to an effective analysis of the white blood cells in the sample by flow cytometry techniques.

In general, two different methods have been developed for providing a white blood cell sample free from interference from red blood cells. IN one method, the white blood cells are isolated and separated from the red blood cells by centrifugation in the presence of a partitioning agent, such as Ficoll-Paque (TM), which is marketed by Pharmacia Fine Chemicals AB, Upsala, Sweden, or a thixotropic gel-like substance. In another method, described in U.S. Pat. No. 4,284,412 to Hansen et al., the red blood cells are lysed to break out the red blood cells into fragments which do not interfere with flow cytometry analysis.

The initial step of separating white blood cells or a subclass thereof from red blood cells is long and arduous; in fact much longer than the relatively simple steps of staining or analyzing the white blood cells or subclass thereof. For clinical purposes, wherein there exists a considerable premium on rapid, repetitive analyses, the necessity of isolating the white blood cells from red blood cells and undesired subclasses of white blood cells is a serious impediment. Furthermore, even for those research applications wherein time is at less of a premium, an initial separation step involves the risk of loss of some of the desired white blood cells during removal of the red blood cells and undesired white blood cells, which introduce uncertainty and inaccuracy to the subsequent analysis. Correspondingly, failure completely to eliminate undesired blood cells from the sample to be analyzed introduces considerable risk of error, and the presence of such undesired cells may well cause errors in the subsequent analysis. Methods involving lysis of the red blood cells are also not wholly satisfactory in that it is difficult to obtain lysis of all the red blood cells without incurring some lysis of the white blood cells.

Presently known and available flow-through cytometers useful for detecting particles, cells and the like, commonly include two channels for the detection of one or more, usually two, subpopulations of cells in a mixture. For example, devices are known which include two fluorescence channels which can detect cells specifically labeled with two immunofluorescent agents associated with the respective fluorescence channels. In these known devices, a complete fluorescence channel including the electrical circuitry and fluorescence detector is used for each category of fluorochrome-treated cells to be detected in the mixture of cells in the sample being analyzed. Therefore, to detect multiple subpopulations of cells in a sample using flow-through cytometry, an equivalent number of fluorescence channels is used. A separate light source, such as a laser, may be used to excite each different type of fluorochrome or immunofluorescent stain which has been tagged. Apparatus utilizing two lasers for analyzing immunofluorescent stains are described in U.S. Pat. Nos. 3,826,364 and 4,284,412.

Analysis and quantifying of two different immunofluorescent stains in a single sample can also be performed with two or more fluorochromes which are activated by a single light source but which have different emission characteristics.

In the field of hematology in general, and in the specific field of immuno-hematology, it is desirable to determine the count of a variety of white blood cells which circulate in the peripheral blood. Subclassification of cells is performed, and the count of the subclasses is of great interest in the evaluation of immune related disease, such as the recently recognized acquired immune deficiency syndrome (AIDS). In particular, the subclasses of the lymphocyte, a mononuclear type of white blood cells in blood, has become of great clinical significance.

There are many instances when it is desirable to be able to directly detect distinct multiple subpopulations of white blood cells of interest from a sample. For instance, in performing certain tests on blood, it may be desirable to detect or quantify the total population of lymphocyte cells in the blood sample and to determine the proporation of T-cells and B-cells as a percentage of the lymphocyte population. Similarly, the detection and quantification of other different types of lymphocytes, such as the helper cell/suppressor cell subset of T-cells and the suppressor cell/natural killer cell subset of T-cells, may be desired. With this in mind, the present invention is directed to satisfying the desired need for the direct determination of subpopulations of white blood cells of interest from a sample mixture without interference from red blood cells.

It is, accordingly, a primary object of the present invention to provide a method for identifying and enumerating a set of blood cells, particularly white blood cells, and specific subclasses of the set of blood cells, while avoiding the necessity for prior separation or lysis of interfering blood cells, particularly red blood cells. It is another object to provide a method for analysis of white blood cells and subclasses thereof which substantially prevents faulty analysis due to the presence of other cells, such as red blood cells, or loss of data through loss of cells from the sample. It is a further object to provide such methods wherein the speed and relative simplicity involved renders blood cell subclass identification and enumeration a viable clinical tool.

SUMMARY OF THE INVENTION

In accordance with the principles of the present invention, a number of advantages and objectives are attained. Primarily, the present invention permits the detection and quantification of subpopulations of white blood cells of interest in a sample without interference from red blood cells or white blood cells in the sample which are not of interest.

Proper preparation of a blood sample in accordance with the principles of the present invention essentially involves providing at least two tagging agents, such as labelled antibodies, which are selective for at least a set of blood cells and a subclass of interest within the set. Preferably, the tagging agents possess the characteristic of emitting fluorescent light upon illumination by a suitable incident light source. In one approach, whole blood from normal human donors is anticoagulated (for example with EDTA) and is incubated with suitable tagged antibodies. The sample is then ready for flow cytofluormetric analysis by detection of light emitted by the tagged antibodies. The detection is limited by gating on a threshold value based on a predetermined intensity of light emitted by one of the antibodies. In the event that indirect immunofluorescent staining is involved, a second incubation is conducted with a second antibody to the first antibody, which in turn has the requisite fluorescent characteristics. For example, white blood cell subpopulations of interest can be determined by the passage of samples tagged with at least two antibodies having predetermined but different fluorescent response through a two laser flow cytometer. By selecting fluorescent labels which, through sufficiently separated in fluorescent wavelength to provide distinguising characteristics, are close enough in spectral range to be excited by a single light source, dual color immunofluorescence results comparable to the two laser excitation mechanism can be achieved with the single light source.

DETAILED DESCRIPTION

While this invention is satisfied by embodiments in many different forms, there is shown in the drawings and will herein be described in detail a particular embodiment of the invention, with the understanding that the present disclosure is to be considered as exemplary of the principles of the invention and is not intended to limit the invention as determined by the appended claims and their equivalents.

The present invention provides a method for identifying and enumerating cells of a subclass of leucocytes in relation to cells of another subclass of leucocytes in a sample containing erythrocytes. In the method, an aliquot of a blood sample is provided. A first set or subclass of leucocytes is identified by measurement of a first physical parameter associated with the first subclass. Preferably the first subclass is selectively tagged by incubating the aliquot in the presence of a first tagging agent, such as an antibody, lectin, nucleic acid dye or membrane potential dye, which is selectively reactive with cells of the first set or subclass. The first tagging agent has a predetermined fluorescence response to optical stimulation. A second subclass of leucocytes is identified by measurement of a second physical parameter associated with the second subclass. Preferably, the second subclass is selectively tagged by incubating the aliquot with a second tagging agent which is selectively reactive with cells of the second subclass. The first subclass of leucocytes and the second subclass of leucocytes may be tagged either sequentially or simulataneously. In some cases a physical parameter of a subclass of leucocytes, such as size, may be used to distinguish the first subclass or the second subclass, by measurement of an associated physical parameter, such as light scatter. In such cases, a second incubation step may not be required.

When the physical parameter being measured is fluorescence response by the first subclass and the second subclass to optical stimulation, the second tagging agent has a predetermined fluorescence response to optical stimulation which is different from the fluorescence response of the first tagging agent. The incubated aliquot is passed substantially a cell at a time, through an area of optical stimulation for both the first tagging agent and the second tagging agent. Light emitted from the first tagging agent and the second tagging agent is detected and data is captured. The data captured is restricted to a predetermined range based on the response of a selected physical parameter, such as fluorescent intensity. Such predetermined range is established by the intensity of the physical response conferred on the cells of interest by at least one of the tagging agents. Cells of the first subclass of cells are differentiated from cells of the second subclass of cells based on the occurrence of predetermined measurement of a physical parameter, such as fluorescence, conferred by the first tagging agent and the second tagging agent.

It should be understood that the tagging agents of the present invention must have measurable physical properties which permit simultaneous use of two or more tagging agents. If the physical property being measured is emission of light activated by optical stimulation, the tagging agents must have emission properties such that the emission spectra can be distinguished.

The tagging agents are preferably antibodies, particularly monoclonal antibodies. Other suitable tagging agents are lectins, nucleic acid dyes, such as propidium iodide and LDS 751 and membrane potential dyes, such as cyanine dyes. Some tagging agents, such as antibodies, react with antigenic sites on the surface of the cells. Other tagging agents, such as nucleic acid dyes and membrane potential dyes, are absorbed by a specific cellular component so as to mark the subclass of cells of interest.

The predetermined fluorescence of certain tagging agents which do not spontaneously emit detectable light (such as antibodies) may be obtained by coupling a marking agent to the tagging agent. Some tagging agents (such as nucleic acid dyes and membrane potential dyes) have fluorescent properties and spontaneously emit detectable light upon optical stimulation. For such cases a coupled marking agent is not required. The marking agents are preferably fluorochromes which have an emission-spectra having sufficient wavelength separation to permit detection of two colors. In general, the fluorochromes should emit fluorescence in the range of from about 10 to about 300 nm above the excitation wavelength. One suitable pair of marking agents has been found to be phycoerythrin, a phycobiliprotein which emits fluorescence at 570 nm and fluorescein, which emits at a wavelength of 530 nm. Three or more suitable tagging agents can be used if they have suitable emission properties or are tagged with markers having suitable emission properties. One suitable group of three marking agents for marking antibodies are phycoerythrin, fluorescein and taxes Red TM which emits fluorescence at 615 nm. One or more of these marking agents may be used in combination with a nucleic acid dye, such as LDS 751, marketed by Exciton Corp., Dayton, Ohio.

The incubated aliquot is passed through a flow cytometry apparatus at a white blood cell flow rate that is substantially equivalent to the white blood cell flow rate that is normally used for samples wherein the red blood cells are removed or lysed. In general, flow rates of from about 20 to about 2000 white blood cells/sec. are suitable. Preferably, the aliquot is passed through the flow cytometry apparatus without lysis or separation of any class of blood cells. It should be understood, however, that the principles of the present invention are equally suitable for the analysis of blood cell fractions provided by lysis or separation of specific subclasses of blood cells from the sample under investigation.

The sets of blood cells of interest which can be distinguished by the method of the invention include nucleated cells, white blood cells, lymphocytes, grunulocytes, monocytes, T-cells, B-cells and natural killer/large granular lymphocyte (NK/LGL) cells. Subclasses of interest within one or more of these sets which can be distinguished by the method of the invention include lymphocytes, granulocytes, monocytes, helper T-cells, inducer T-cells, suppressor T-cells, cytotoxic T-cells, T-cells, T-cells in maturation/activation stages, B-cells, B-cells in maturation/activation stages, monocytes in maturation/activation stages, neutrophils, basophils, eosinophils and granulocytes in maturation/activation stages, NK/LGL cells and NK/LGL cells in maturation/activation stages. Of course, the method of this invention can be used to distinguish and compare two or more of the sets enumerated hereinabove.

By suitable selection of a tagging agent and a marking agent, if required, the sets and subclasses can be investigated in reference to each other in a vast array of combinations. For example: if the set is white blood cells, the subclass can be lymphocytes, granulocytes, monocytes and combinations thereof; if the set is lymphocytes, the subclass can be T-cells, subclasses of T-cells, B-cells, subclasses of B-cells and combinations thereof; if the set is T-cells, the subclass can be any subclass of T-cells or a combination thereof; if the set is granulocytes, the subclass can be neutrophils, eosinophils, basophils, maturation stage granulocytes and combinations thereof.

The principals of the method of the present invention are suitable for analysis of subclasses of blood cells by many varied techniques. Physical properties other than fluorescence, such as light scatter and acoustic absorption can be used as tagging agents. An automated scanning microscope can be used to examine the tagged blood sample a cell at a time to provide the subset analysis in accordance with the invention. A preferred tagging agent is the use of fluorescent marking agents and the preferred apparatus is a flow cytometry device as described hereinbelow.

Figure 1:
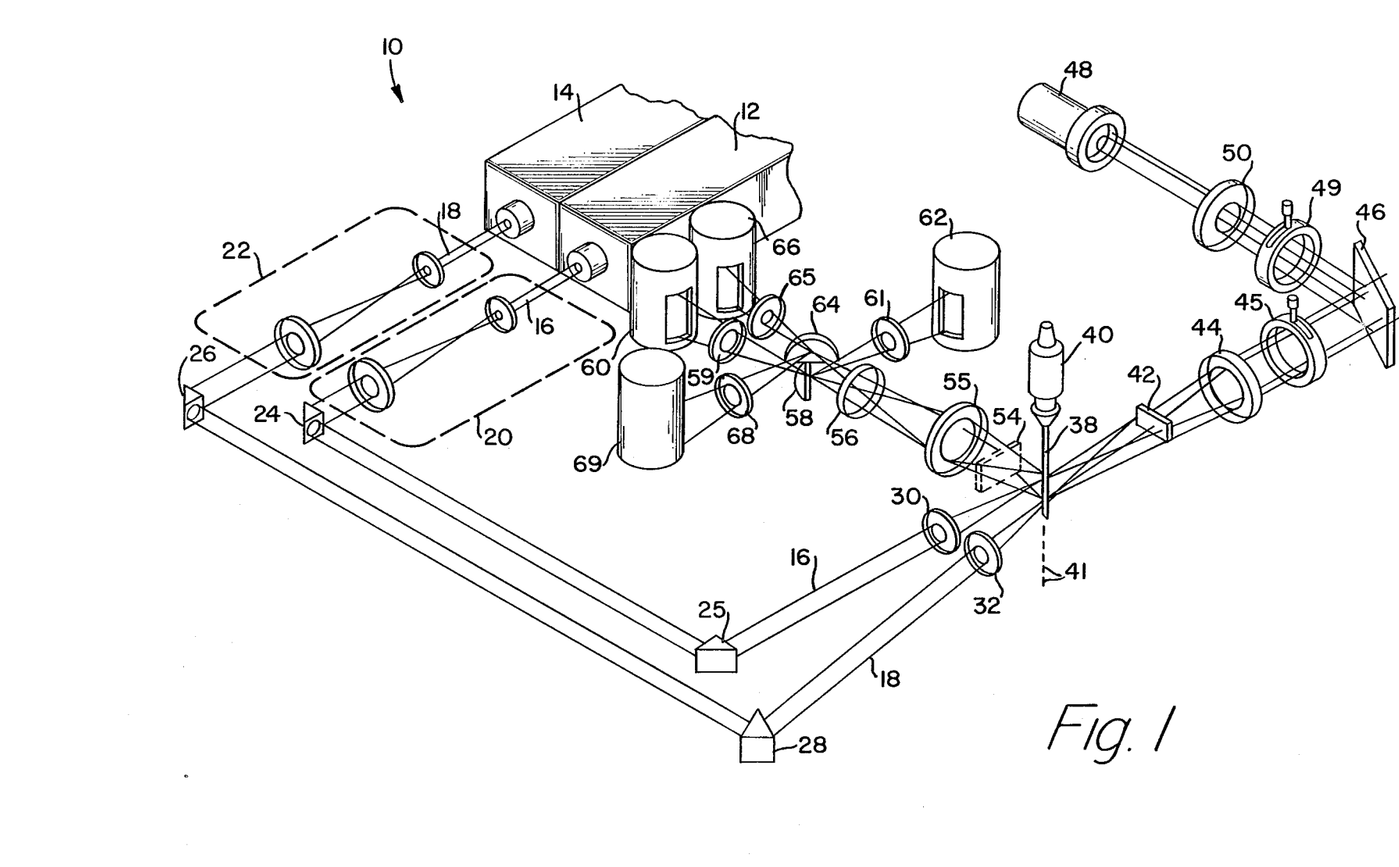
FIG. 1 is a schematic illustration of one embodiment of the optical elements and light paths of a flow cytometry device which are useful for determining fluorescence related to multiple subpopulations of particles in a flow path.

In FIG. 1 the optical and particle flow elements of a flow cytometry device 10 are illustrated. The optical and flow elements of FIG. 1 represent the major components of a flow cytometry instrument for flowing particles in a liquid stream, substantially one at a time, in order to analyze those particles for specific characteristics thereof. For example, the elements of the device of FIG. 1 may be included in a FACS (Trademark) fluorescence-activated sorter, manufactured and sold by the FACS System Division of Becton, Dickinson and Company, Sunnyvale, Calif. The FACS cell sorter analyzes and separates cell populations on the basis of light scatter and fluorescence in a wide variety of research laboratory applications. In addition to the optical and flow elements to be described in more particular detail herein, and which may be embodied in an instrument such as the FACS cell sorter, other details of a cell sorting apparatus useful in conjunction with the present invention are described in U.S. Pat. No. 3,826,364. It is understood that the present invention is useful in many different types of flow cytometry devices, whether measuring light scatter, particle volume, fluorescence or any other optical parameters for the identification or quantification of subpopulations of particles in a sample.

As illustrated in FIG. 1, light energy is provided for the flow cytometry device by a suitable light source, 12 and 14, such as a laser. In the embodiment being described, two sources of light are provided in flow cytometry device 10 so that it is possible to detect and quantify a plurality of different types of particles having different fluorescence characteristics. It is understood, however, that the inclusion of two lasers in the embodiment illustrated in FIG. 1 merely serves as an exemplary embodiment employing more than one light energy source and analysis elements in the type of invention being described. The elements of the present invention may be utilized just as satisfactorily if only one light source is employed in the flow cytometry apparatus. Also, it should be understood that a coherent light source, such as a laser, is not required. Other light sources, such as a mercury vapor lamp, are suitable and are preferred for some applications. Similarly, more than two light sources may be utilized.

In the present invention, lasers 12 and 14 are selected to produce primary emissions of coherent light at specific wavelengths separated from each other in the spectral range. For example, laser 12 is preferably selected to operate in the blue/green spectral region whereby fluorochromes, which fluoresce when irradiated by optical stimulation of certain wavelengths, attached to particles passing through the light generated by laser 12 will become excited. One such laser useful for the present invention is an argon ion laser having a primary emission at 488 nanometers (nm). Laser 14 is preferably selected to operate at a different, separated wavelength from laser 12. Particles having fluorochromes thereon which fluoresce when irradiated by optical stimulation of the wavelength of laser 14 will become excited when these particles pass through the light generated by laser 14. The operation of laser 14 may cover the yellow/red region of the visible spectrum so as to be substantially separated in wavelength from the spectral region of laser 12. One such laser which satisfies this requirement is a Rhodamine 6-G dye laser which can be turned to have a primary emission at 595 nm. It is desirable that the difference in wavelengths of the two lasers be substantial enough to be outside of the spectral range for exciting at least two fluorochromes with each laser. It has been found that a difference in wavelengths between the two lasers of 75 to 300 nm will permit the desirable result just described. Of course, the selection of the fluorochromes or other quantifiable marking agents must be compatible with the lasers which are used in the present invention so that up to two fluorochromes may be excited by the light energy provided by each laser.

Emerging from lasers 12 and 14, each beam 16 and 18, respectively, may pass through beam expanders schematically indicated by numerals 20 and 22 which enlarge each beam while retaining the parallel character thereof. As each beam emerges from the beam expander, which is preferable but not necessary for operation of the present invention, it normally must have its direction changed due to space requirements in the flow cytometry device. To this end, beam 16 is reflected through prisms 24 and 25, while beam 18 is reflected through prisms 26 and 28. All of these prisms may be made adjustable to properly align the beams during operation.

After beams 16 and 18 pass through the prisms, they are directed toward lenses 30 and 32 for focusing the beams onto the stream of particles. While lenses 30 and 32, if employed, are selected in accordance with the type of flow cytometry device being employed, these lenses may be selected in accordance with the description thereof in patent application Ser. No. 361,672, filed in the U.S. Patent and Trademark Office on March 25, 1982, and having a common assignee as the present application.

Once the laser beams pass through lenses 30 and 32, they are directed onto particle stream 38. A nozzle 40, incorporated within the flow cytometry device of the present invention facilitates the flowing of particles 41 within fluid stream 38. The utilization of a nozzle of this type is well known and is described, for example, in U.S. Pat. No. 3,826,364. As seen more clearly in FIG. 1, laser beam 16 lies on the optical axis of a light-scatter channel and is used for scatter detection of particles. It is understood, however, that the light scatter features herein described are merely included to round out the features of a typical flow cytometry device which may rely upon light scatter to obtain information from particles passing through the light beams and are not required for practice of the present invention.

Thus, light beam 16 is the first light beam encountered by a particle flowing in stream 38 emerging from nozzle 40. Thereafter, beam 16 strikes the light-scatter obscuration bar 42 on the optical axis of the light-scatter channel. Scattered light collected by the lens 44, passes through a first iris 45 which determines the maximum angle of scattered light collected. Following first iris 45 is a beam splitting mirror 46 which reflects a percentage of the incident light toward scatter detector 48, and transmits the remaining percentage of the incident light onto a light absorber (now shown). A second iris 49 functions as a field stop to restrict the source of scattered light to the point of intersection of laser beam 16 and stream 38. After passing through filter 50, the scattered light is detected in detector 48. This detector functions electrically to assess the size of the particles flowing in the fluid stream according to well known techniques.

Laser beam 18 is also directed at flowing steam 38, but is vertically displaced from laser beam 16 along the vertical axis of the stream. Light from beam 18 scattered by a particle is picked up by the scatter-channel optics, but preferably blocked from detector 48 by the dielectric filter placed in the scatter channel.

With respect to the fluorescence channels, illumination provided by the different wavelength operation of the lasers is available for sequential excitation of fluorochromes having predetermined, separated emission spectra. Up to two fluorochromes having predetermined, separated emission spectra are excited by the excitation energy provided by the light energy of each laser. As seen in FIG. 1, the two independent laser beams intersect stream 38 at points vertically spaced so that a particle crosses laser beam 16 first and then laser beam 18. Accordingly, two pairs of optical signals may be generated by the particles passing through each of the light beams to provide a total of four optical signals. These pairs of signals are preferably spaced in time by the time required for the particle to travel from the first beam intersection point to the second beam intersection point. This time spacing permits the pairs of signals to be separately analyzed giving signals proportional to the fluorescence emissions of the particles when excited at the two different excitation wavelengths. Fluorescence signals emitted from the particles are directed around obscuration bar 54 which blocks refracted light from the separated beams. All fluorescence signals are focused by lens 55 preferably through a first filter 56 which permits light only at specific wavelengths to pass therethrough.

Fluorescence emitted by particles stimulated by light beam 16, after passing through filter 56, then encounters a dichroic mirror 58. The purpose of dichroic mirror 58 is to separate two different colors traveling along the fluorescence light path so that they can be analyzed separately. For example, dichroic mirror 58 would be selected to separate, for example, the different color wavelengths of particles excited by light beam 16 produced only by laser 12. For instance, wavelengths in the blue region would be transmitted through dichroic mirror 56 and then through a barrier filter 59 which is designed to transmit wavelengths of only one color region, in this instance blue. Blue light then enters a fluorescence detector 60.

Light encountering dichroic mirror in the green color region would be reflected by the dichroic mirror through a barrier filter 61 which transmits wavelengths of only one color region, in this case, green. A fluorescence detector 62 then receives this green light.

Light beam 18 also provides excitation energy at a single wavelength sufficient to excite up to two fluorochromes different from those excited by light beam 16. After the fluorescence emitted by the particles excited by light beam 18 passes through lens 55 and first filter 56, this light encounters another dichroic mirror 64. Similar to the description of dichroic mirror 58, the second dichroic mirrow 64 is selected to separate the wavelengths of two different regions of the color spectrum. For example, both yellow and red signals may be generated as a result of the single excitation source provided by light beam 18 directed from laser 14. Wavelengths in the yellow region would be transmitted through dichroic mirror 84 and then through a barrier filter 65 which is designed to transmit wavelengths of only the yellow region. This light is then directed to a fluorescence detector 66. Wavelengths in the red region would be reflected by dichroic mirror through a barrier filter 68, whereupon this light enters fluorescence detector 69. Accordingly, it can be seen that light from two lasers, which can excite up to two different fluorochromes at the respective wavelengths of operation of each, allows the detection and quantification of multiple subpopulations of particles in a sample during a single pass of that sample in a flow cytometry device such as described.

Fluorescence detectors 60, 62, 66 and 69 are provided to preferably receive the four separated blue, green, yellow and red light paths, respectively. These fluorescence detectors may be low-noise photomultiplier tubes or the like which convert optical signals into electrical siognals. These electrical signals are then fed electrically to be processed by the electronics (not shown) of the flow cytometry device for analysis or other purposes. Various displays, information presentation, accumulation or recordation may be provided in the flow cytometry device. In accordance with one embodiment of the invention a computer 71 is provided to retain the results of the analysis to provide the direct identification of a subpopulation of cells in the form of a plot or table. When two antibodies are used, a two dimensional plot is generated. For three antibodies a representational three dimensional plot can be generated showing white blood cell subpopulations to cloud-like formations.

The instrument is aligned and calibrated for cell subset analysis by cell surface immunofluorescence. Unstained lymphocytes or microspheres with the same background fluorescence as lymphocytes are run at a rate of from about 500 to about 1500/sec. When a stable flow rate is established all threshold levels are set to maximum. No counts are recorded at this point. The threshold level for the parameter identifying the cells of interest, i.e. for green fluorescence, is then lowered until 1 to 5 counts per second are observed. The instrument is now ready for the analysis of unlyzed whole blood samples stained according to the method of the invention.

Operation of the present invention will now be described in conjunction with the following examples for illustrative purposes only. The examples exemplify, but do not limit the scope of the technique for detecting, distinguishing and/or quantifying multiple subpopulations of particles in a sample.

EXAMPLE 1

Human blood was obtained from volunteers. 50 l. of blood was incubated with 5 $\mu$l each of two monoclonal antibodies commercially available from Becton Dickinson and Company for 30 min. at 4° C. The monoclonal antibodies were anti-Leu 2a, coupled to phycoerythrin (PE), and anti-Leu 3a, coupled to fluorescence isothiocyanate (FITC). Anti-Leu 2a is specific for the subclass of T-cell suppressor-cytotoxic cells. Anti-Leu 3a is specific for the subclass of T-cell helper-inducer cells. Another sample of the blood was lysed with an ammonium chloride buffer that selectively lyses red cells and not white cells. This sample was combined with 5 $\mu$l each of the above monoclonal antibody reagents (anti-Leu-2a-PE and anti-Leu-3a-FITC) and incubated for 30 min. at 4° C.

Figure 2A:
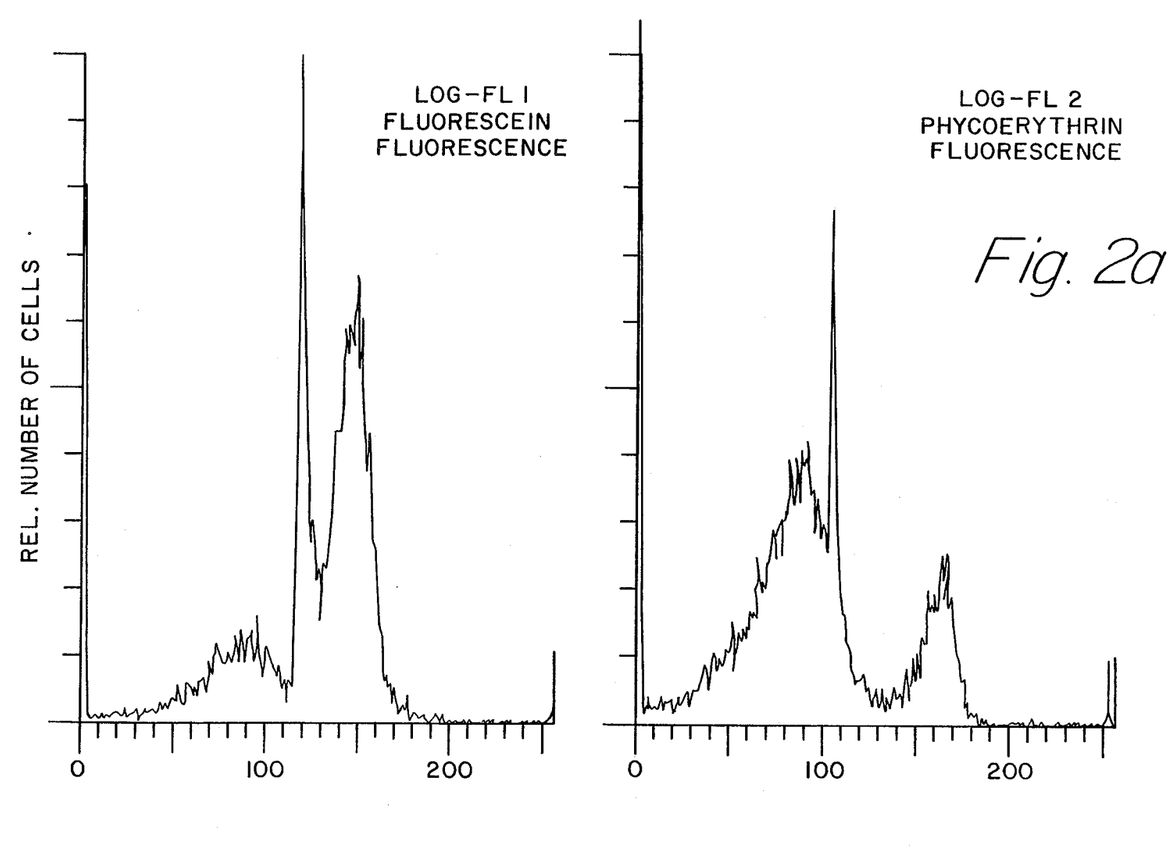
FIGS. 2-5 are a graphic representation of the detection and quantification of subpopulations of white blood cells in a sample determined by a passage through a flow cytometer of a blood sample containing white blood cells and unlysed red blood cells in accordance with the principles of the present invention.

Both preparations were washed by adding phosphate saline (buffer) to provide a final volume of 2 ml and centrifuging at 100 xg for 5 min. The supernatant was then removed and the cells were suspended in 1 ml of buffer. The analysis for subsets was performed with a Becton Dickinson and Company FACS Analyser equipped with a two color fluorescence detection system. Both samples were passed through the FACS analyser at a rate of 50 white blood cells per second. The triggers for the acquisition of digital data were green and red-fluorescence thresholds combined in a non-exclusive OR logic. A histogram of the number of cells vs. the fluorescence intensity was created using a ND64 pulse height analyser as shown in FIG. 2a. The brightest populations in green and red fluorescence are the anti-Leu 3 and anti-Leu-2 stained cells. Their ratio is relevant for medical diagnosis. For a typical blood sample a ratio of leu-3/leu-2 of 2.6 was found for the unlysed whole blood sample, based on 9266 cells; a separate lysed sample yielded a ratio of 2.9 based on 17937 cells.

Figure 2B:
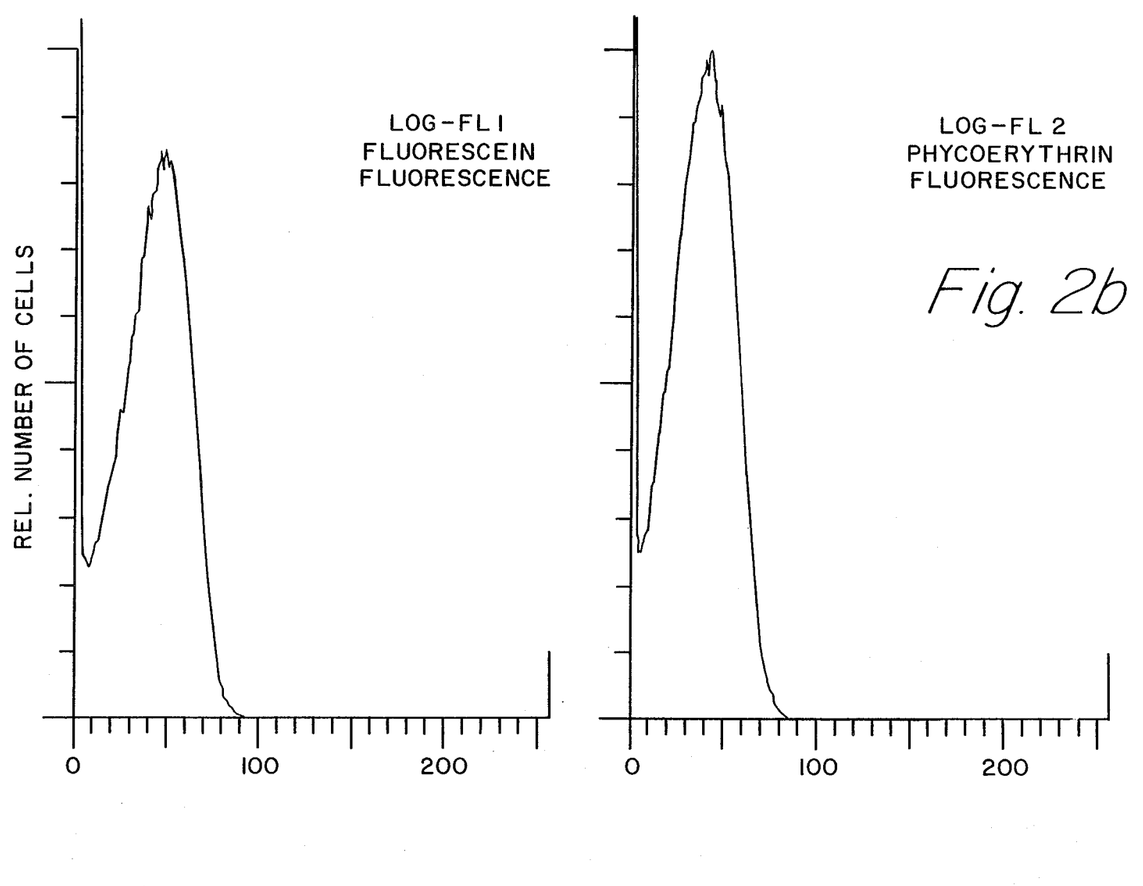

FIG. 2b shows data obtained with the same sample using a volume or scatter trigger, which is normally used. Because of their excess over white cells, only red cell fluorescence is visible in the histogram.

EXAMPLE 2

Figure 3:
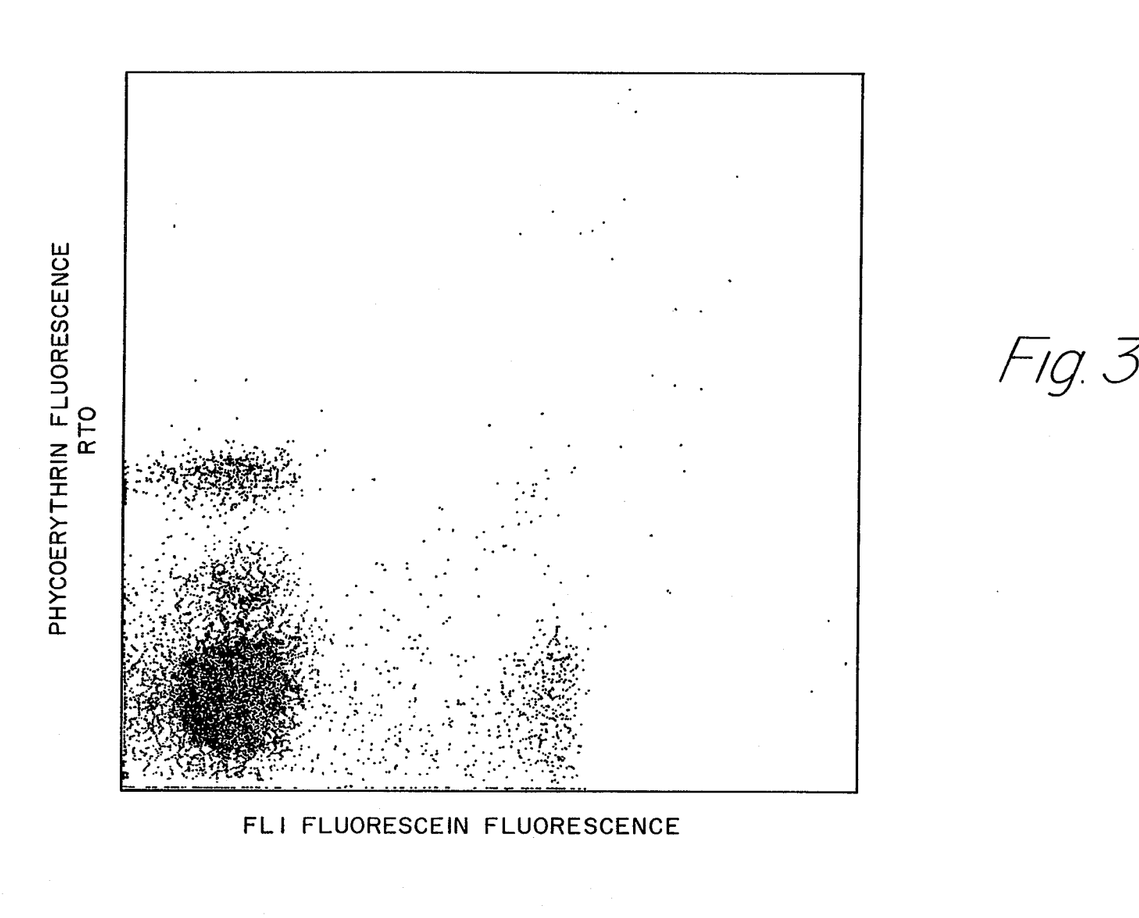

Human blood was obtained as in Example 1. 5 $\mu$l of anti-Leu-3a-PE and 5 $\mu$l of anti-Leu-2a-FITC were placed into a 12×75 mm2 tube and phosphate buffered saline containing a 0.1% sodium azide was added to a total volume of 50 $\mu$l. To these antibodies 50 $\mu$l of the unlyzed blood was added. The mixture was incubated for 30 min. at 4° C. Buffer was added to a final volume of 1 ml and subsequently 4 $\mu$l of a saturated methanolic solution of the laser dye LDS 751 from Exciton (Dayton OH) were mixed in. The sample was analyzed with a FACS flow cytometer, provided with a 488 nm Ar ion laser for excitation only equipped with 3 photomultipliers for fluorescence and detection at a rate of about 200 white cells/sec. The LDS 751 fluorescence of white cells was used as a gate for data capture. Data were stored in cell by cell list-mode, using a FACS Consort 30 data system. FIG. 3 shows that anti-Leu-2a-FITC and anti-Leu-3a-PE stained cells can be clearly identified.

EXAMPLE 3

Figure 4:
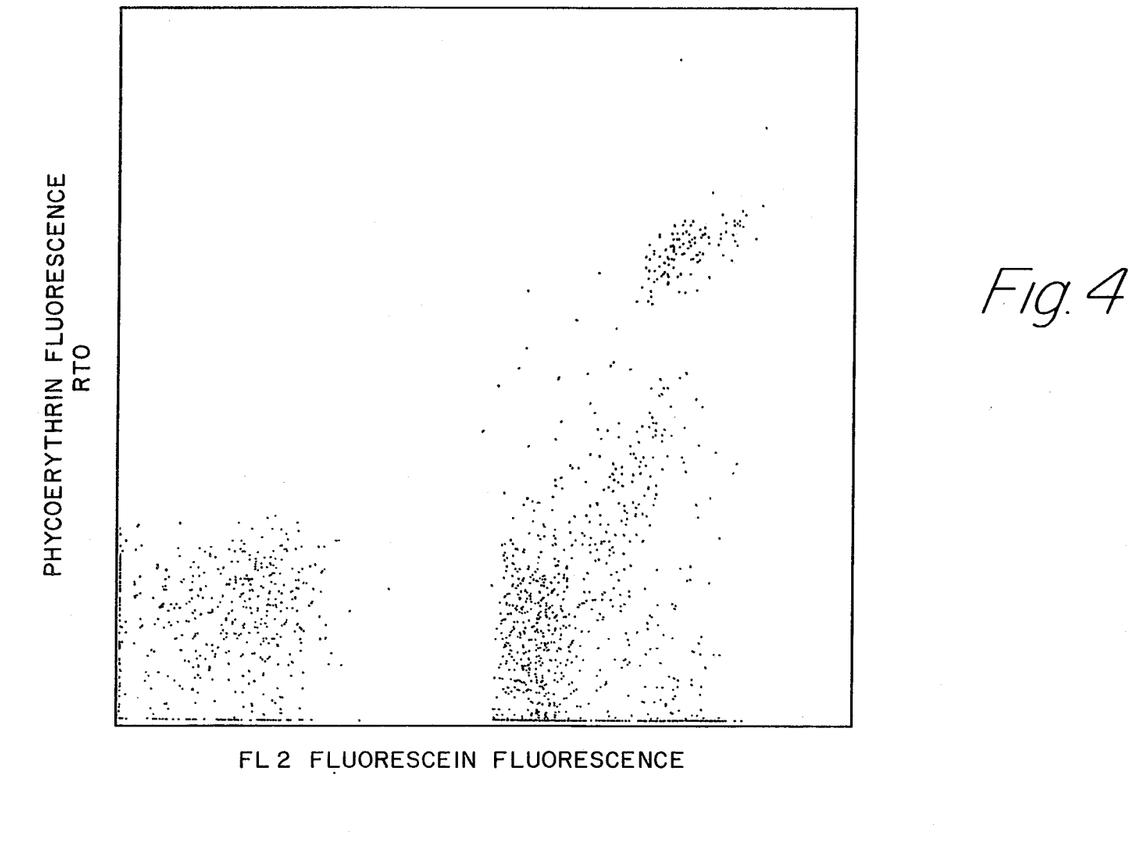

Human blood was obtained as above. Staining was performed as in Example 2 using anti-HLe-1-FITC and anti-Leu-3a-PE as antibodies. Anti-HLe-1 is a monoclonal antibody which is specific for all white blood cells. The sample was washed once by centrifuging the cells at 200 xg and resuspending them in 1 ml of buffer. Analysis was performed with a FACS instrument at rates of 500 to 1000 tagged white blood cells per second. Fluorescence was excited using an Ar ion laser at 488 nm. The fluorescence of white cells stained with HLe-1-FITC was used as a trigger signal. FIG. 4 shows that white cell subsets can be clearly identified. Note that anti-HLe-1 splits white cells into three subsets by fluorescence intensity. In independent experiments these subsets have been identified as granulocytes, monocytes and lymphocytes.

The population in the lower left hand corner of the dot-plot represents red cells. A short scatter trigger period was used to generate these dots to demonstrate the excellent separation between red and white cells based on anti-HLe-1-FITC fluorescence.

EXAMPLE 4

Figure 5A:
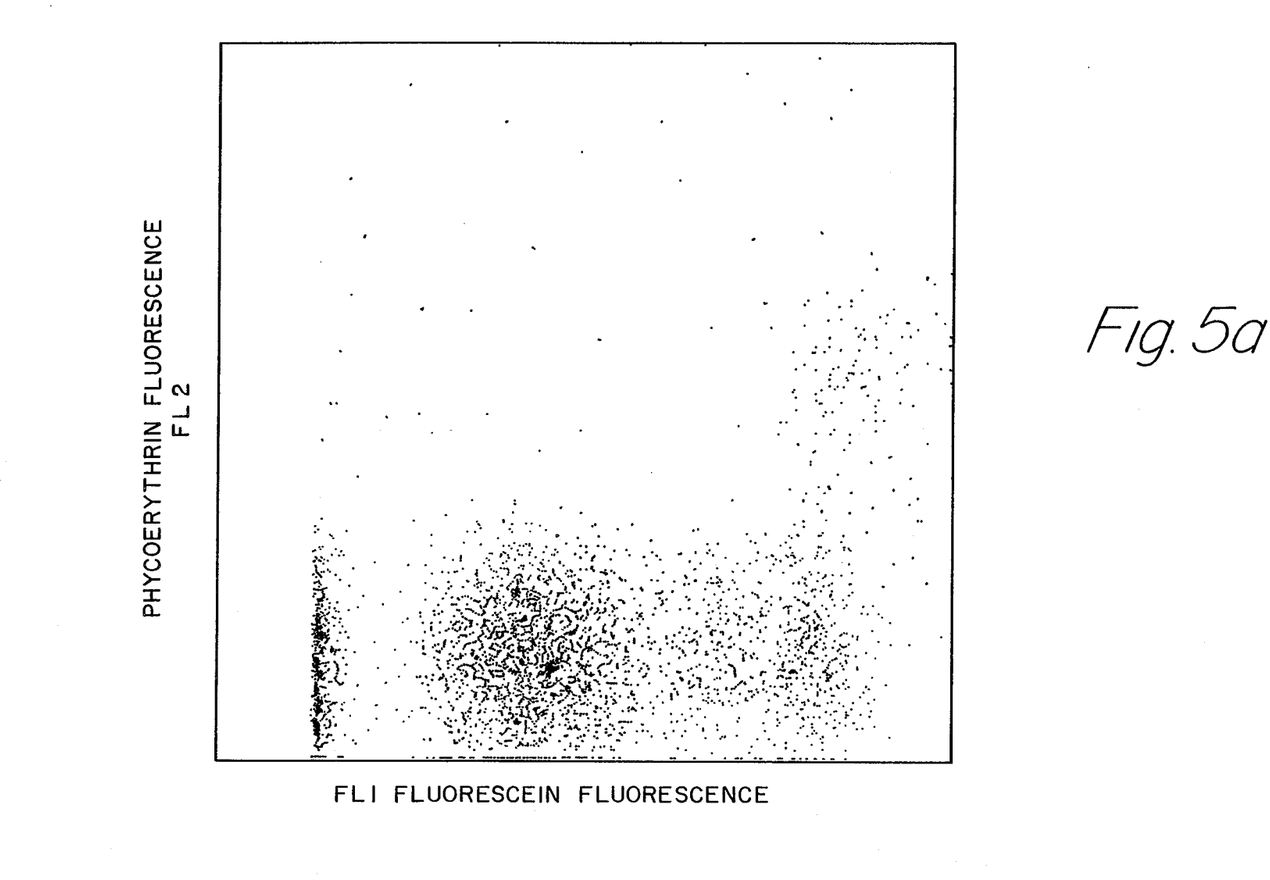
Figure 5B:
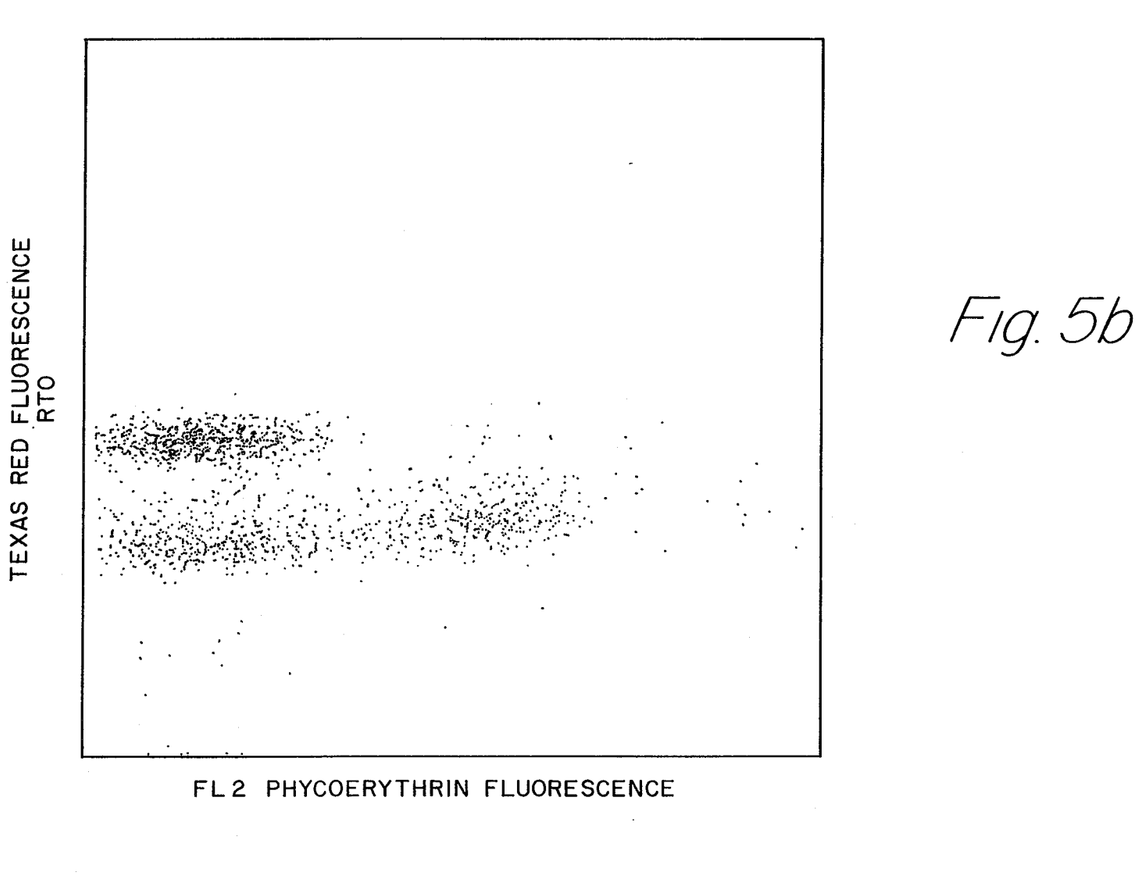
Figure 5C:
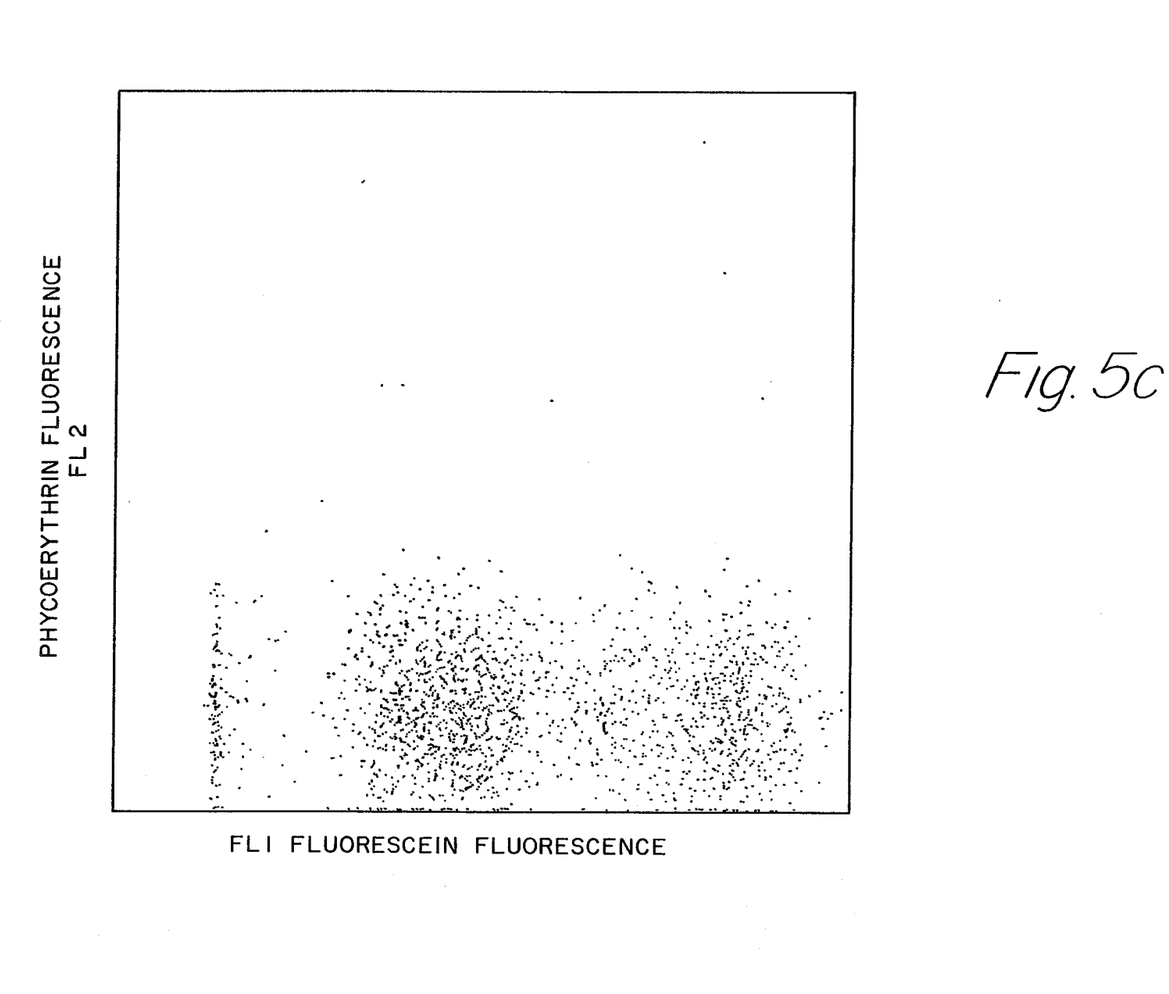
Figure 5D:
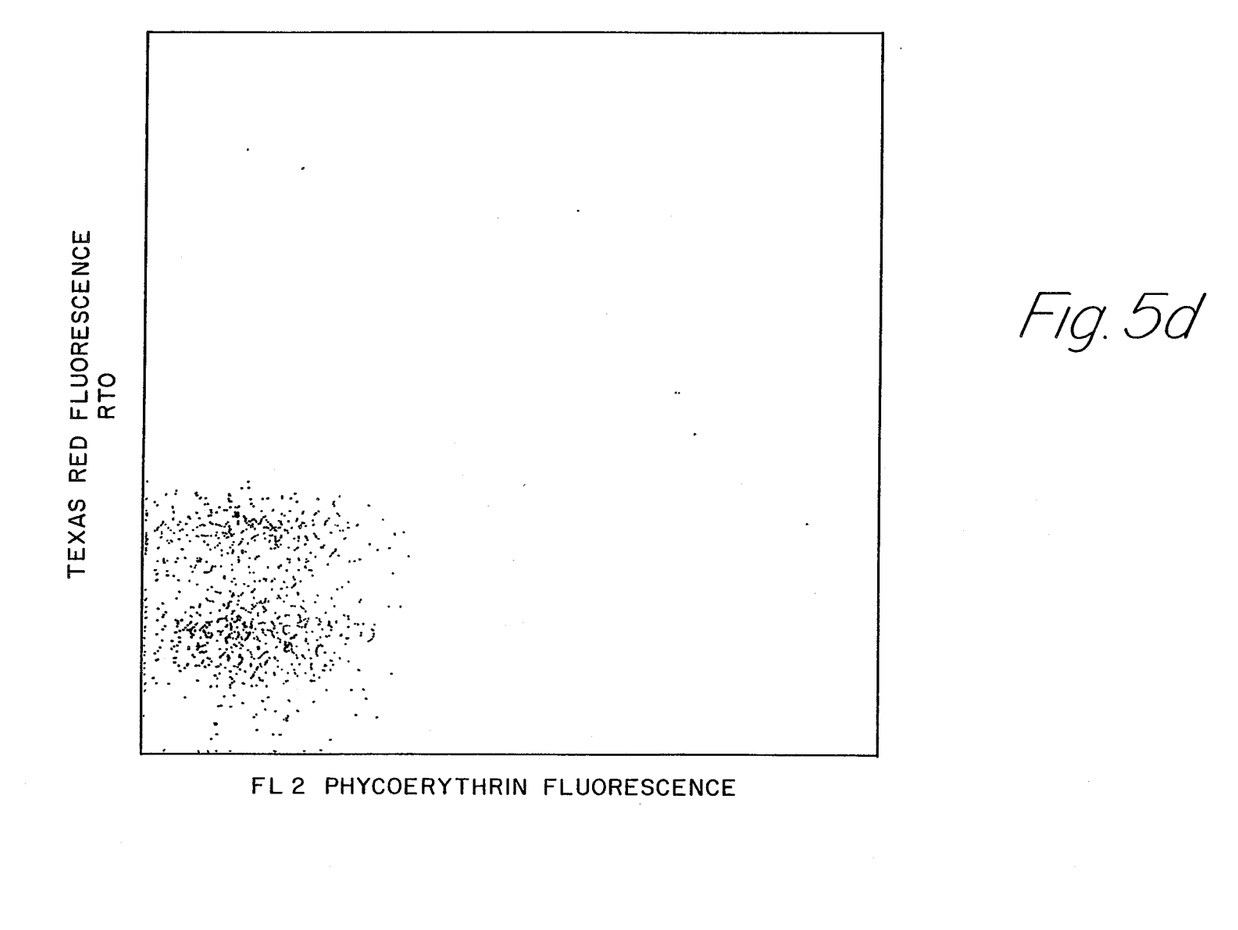

The staining procedure was as described in Example 3. However, three anti-cell surface monoclonal antibodies each tagged with its own chromophore were used for the staining. To enable the detection of Texas Red TM, a FACS flow cytometer equipped with two lasers, an Argon ion laser and an Argon ion pumped dye laser set to 590 nm was used. FIG. 5a and 5b show the pattern obtained with anti-HLe-1-FITC, anti-Leu-2a-PE and anti-Leu-3a with texas red, where FL1 is FITC, FL2 is PE and SSC is Texas Red TM. FIGS. 5c and 5d show the pattern of a control sample stained with anti-HLe-1-FITC alone.

Table 1 compares percentage data obtained using the method of the invention with data obtained using a blood lysis method and a Ficoll Paque isolation method for obtaining mononuclear cells. The comparison shows that data obtained with the method of the invention compares with the Ficoll Paque data, and the lysing method; both techniques which are well established and accepted for lymphocyte subset analysis.

TABLE 1

Comparison of white cell subset fractions obtained with different methods.

|  | Whole Blood | NH4Cl lysed blood | Ficol Hypaque prep. of lymphocytes |
|---|---|---|---|
| leu-3a | 48 ± 2% | 48 ± 5% | 50 ± 5% |
| leu-2a | 21 ± 1% | 30% | 23 ± 2% |

What is claimed is:

1. A method for identifying and enumerating cells of a subclass of blood cells in relation to cells of another subclass of blood cells comprising the steps of:
   (1) providing an aliquot from a blood sample,
   (2) selectively tagging cells of a first subclass of blood cells by incubating said aliquot with a first tagging agent which is selectively reactive with cells of said first subclass, said first tagging agent having a measurable physical response to suitable stimulation;
   (3) selectively tagging cells of at least a second subclass of blood cells by incubating said aliquot with a second tagging agent which is selectively reactive with cells of said second subclass, said second tagging agent having a measurable physical response to suitable stimulation;
   (4) analyzing said aliquot, substantially a cell at a time, by subjecting said aliquot to suitable stimulation for both said first tagging agent and said second tagging agent while detecting said measurable physical response provided by said first tagging agent and said second tagging agent and capturing the data provided by said detection, said captured data being restricted to a predetermined range exceeding a threshold of a physical response value established by the intensity of the physical response conferred on the cells of interest by at least one of said tagging agents, and
   (5) differentiating cells of said first subclass of cells from said second subclass based on occurrence of said measurable physical response of said first tagging agent and said second tagging agent.

2. A method in accordance with claim 1 wherein said first tagging agent and said second tagging agent have a predetermined fluorescent response to optical stimulation.

3. A method in accordance with claim 2 wherein said aliquot is analyzed by passing said aliquot through an area of optical stimulation while detecting light emitted from said first tagging agent and said second tagging agent.

4. A method in accordance with claim 1 wherein said first subclass of blood cells is a set of white blood cells and said second subclass is a group of white blood cells within said set.

5. A method in accordance with claim 1 wherein said first and second tagging agents are selected from the group consisting of antibodies, lectins, nucleic acid dyes and membrane potential dyes.

6. A method in accordance with claim 1 wherein said first and second tagging agents are monoclonal antibodies.

7. A method in accordance with claim 1 wherein at least one of the group consisting of said first tagging agent and said second tagging agent is reactive with distinct antigenic determinants of a subclass of cells of interest.

8. A method in accordance with claim 1 or claim 6 wherein said first subclass is selected from the group consisting of nucleated cells, white blood cells, lymphocytes, granulocytes, T-cells, B-cells and NK/LGL cells and said second subclass of blood cells is selected from the group consisting of lymphocytes, granulocytes, monocytes, helper T-cells, inducer T-cells, suppressor T-cells, cytotoxic T-cells, T-cells, B-cells, T-cells in maturation/ activation stages, B-cells in maturation/activation stages, monocytes in maturation/activation stages, neutrophils, basophils, eosinophils and granulocytes in maturation/activation stages and NK/LGL cells in maturation/activation stages.

9. A method in accordance with claim 1 or claim 2 wherein at least a third subclass of blood cells is selectively tagged by incubating said aliquot with a third tagging agent which is selectively reactive with cells of said third subclass, said third tagging agent having a measurable physical response to suitable stimulation.

10. A method in accordance with claim 9 wherein said third tagging agent has a predetermined fluorescent response to optical stimulation.

11. A method in accordance with claim 10 wherein said third tagging agent is a monoclonal antibody.

12. A method in accordance with claim 11 wherein one of said tagging agents is a nucleic acid dye.

13. A method in accordance with claim 1 wherein said tagging agents are selected from antibodies, lectins, nucleic acid dyes and membrane potential dyes.

14. A method in accordance with claim 2 wherein said tagging agents are marked with a marking agent selected from the group consisting of phycoerythrin, fluorescein isothiocyanate, Texas Red, allophyocyanine, R-phycocyanin and LDS-741.

15. A method in accordance with claim 3 wherein said aliquot is passed through said area of optical stimulation at a rate of from about 20 to about 2000 white blood cells per second.

16. A method in accordance with claim 1 wherein said first and second subclasses are white blood cells and subclasses thereof and said first and second tagging agents are monoclonal antibodies conjugated to fluorescent marking agents.

17. A method in accordance with claim 9 wherein said first, second and third subclasses are white blood cells and subclasses thereof and at least one of the group consisting of said first tagging agent, said second tagging agent and said third tagging agent is a monoclonal antibody.

18. A method in accordance with claim 1 wherein said incubation steps are performed sequentially.

19. A method in accordance with claim 1 wherein said incubation steps are performed simultaneously.

20. A method in accordance with claim 1 wherein said aliquot is analyzed without lysis or separation of any subclass of blood cells.

21. A method in accordance with claim 1 wherein at least one of said measurable physical responses of said tagging agents is provided by a physical property associated with at least one of said subclasses of cells.

* * * * *